(12) United States Patent
Bayer

(10) Patent No.: US 9,480,779 B2
(45) Date of Patent: Nov. 1, 2016

(54) IMPLANT AND METHOD FOR PRODUCING THE SAME

(75) Inventor: Ullrich Bayer, Admannshagen-Bargeshagen (DE)

(73) Assignee: BIOTRONIK AG, Buelach (CH)

(*) Notice: Subject to any disclaimer, the term of this patent is extended or adjusted under 35 U.S.C. 154(b) by 0 days.

(21) Appl. No.: 13/164,179

(22) Filed: Jun. 20, 2011

(65) Prior Publication Data

US 2011/0318219 A1    Dec. 29, 2011

Related U.S. Application Data

(60) Provisional application No. 61/358,963, filed on Jun. 28, 2010.

(51) Int. Cl.
| | | |
|---|---|---|
| C22C 38/00 | (2006.01) | |
| C22C 38/04 | (2006.01) | |
| A61L 31/02 | (2006.01) | |
| A61L 31/14 | (2006.01) | |

(52) U.S. Cl.
CPC ........... *A61L 31/022* (2013.01); *A61L 31/148* (2013.01); *C22C 38/00* (2013.01); *C22C 38/04* (2013.01)

(58) Field of Classification Search
CPC .............................. C22C 38/00; C22C 38/04
USPC ............. 148/320, 331, 333, 337; 164/70.1; 420/83, 84, 87; 424/422, 423, 426; 623/1.1, 23.64
See application file for complete search history.

(56) References Cited

U.S. PATENT DOCUMENTS

| | | | |
|---|---|---|---|
| 2002/0004060 A1* | 1/2002 | Heublein et al. | ............. 424/422 |
| 2006/0229711 A1 | 10/2006 | Yan et al. | |
| 2008/0140199 A1* | 6/2008 | Briest | ........................ 623/17.11 |
| 2008/0281396 A1 | 11/2008 | Ishida et al. | |
| 2009/0017087 A1* | 1/2009 | Byon et al. | ................... 424/422 |
| 2010/0076544 A1 | 3/2010 | Hoffmann et al. | |
| 2010/0076556 A1* | 3/2010 | Tomantschger et al. | .. 623/11.11 |

FOREIGN PATENT DOCUMENTS

WO          9903515 A2      1/1999

OTHER PUBLICATIONS

EP11168168.0 European Search Report mailed Aug. 6, 2014.

* cited by examiner

*Primary Examiner* — Brian Walck
(74) *Attorney, Agent, or Firm* — Wagenknecht IP Law Group PC

(57) ABSTRACT

The present invention relates to an implant, in particular an intraluminal endoprothesis, the body of which comprises at least predominantly a material with iron as the main constituent. For accelerating the degradation, the material comprises sulfur as first minor constituent with a concentration of more than 0.2% by weight and not more than 1% by weight, preferably not more than 0.5% by weight, and comprises as second minor constituent at least one element of the group which comprises calcium, manganese and magnesium. Furthermore, a method for producing such an implant is described.

17 Claims, No Drawings

IMPLANT AND METHOD FOR PRODUCING THE SAME

CROSS REFERENCE TO RELATED APPLICATIONS

This invention claims benefit of priority to U.S. patent application Ser. No. 61/358,963, filed on Jun. 28, 2010; the contents of which are herein incorporated by reference in their entirety.

TECHNICAL FIELD

The present invention relates to an implant, in particular an intraluminal endoprosthesis, the body of which comprises at least predominantly a material with the main constituent iron, and a method for producing a corresponding implant.

BACKGROUND

Medical endoprostheses or implants for a wide range of applications are known in a large variety from the prior art. Implants in the meaning of the present invention are to be understood as endovascular prostheses or other endoprostheses, for example stents, in particular wire mesh stents, fastener elements for bones, for example screws, plates or nails, medullary nails, spiral bundle nails, Kirschner-nails, wires for septal occluders, surgical sutures, intestinal staples, vascular clips, prostheses in the region of the hard and soft tissue, and anchor elements for electrodes, in particular of pacemakers or defibrillators.

Today, particularly frequently used as implants are stents which serve for the treatment of stenoses (vasoconstrictions). Stents have a body, if applicable, in the form of an open-worked tubular or hollow-cylindrically grid which is open at both longitudinal ends. The tubular grid of such an endoprosthesis is inserted into the vessel to be treated and serves for supporting the vessel. Stents are established in particular for the treatment of vascular diseases. By using stents or other implants, constricted areas in the vessels can be expanded, thereby resulting in a lumen gain. By using stents or other implants, an optimal vessel cross-section, which is primarily necessary for the success of the therapy, can be achieved; however, the permanent presence of such a foreign body initiates a cascade of microbiological processes which can result in a gradual constriction of the stent, and in the worst case in a vascular occlusion. An approach for the solution of this problem is to produce the stent or other implants from a biodegradable material.

Biodegradation is to be understood as hydrolytic, enzymatic and other metabolic-related degradation processes in a living organism which are mainly caused by body liquid which gets in contact with the biodegradable material of the implant and which result in a gradual degradation of the structures of the implant containing the biodegradable material. Through this process, the implant loses its mechanical integrity at a certain point in time. As a synonym for the term biodegradation, the term biocorrosion is frequently used. The terms bioresorption comprises the subsequent resorption of the degradation products by the living organism.

Suitable materials for the body of biodegradable implants can contain, for example, polymers or metals. The body can consist of a plurality of said materials. A common feature of said materials is their biodegradability. Examples for suitable polymeric compounds are polymers from the group cellulose, collagen, albumin, casein, polysaccharides (PSAC), polylactide (PLA), poly-L-lactide (PLLA), polyglycol (PGA), poly-D,L-lactide-co-glycolide, (PDLLA-PGA), polyhydroxybutyrate (PHB), polyhydroxyvaleric acid (PHV), polyalkyle carbonate, polyorthoester, polyethylene terephthalate (PET), polymalonic acid (PML), polyanhydrides, polyphosphazenes, polyamino acids and their co-polymers, and hyalaronic acid The polymers can be available depending on the desired properties in pure form, in derivatized form, in the form of blends or as co-polymers. Metallic biodegradable materials are primarily based on alloys of magnesium and iron. The present invention relates preferably to implants, the body of which consists primarily of a biodegradable material with iron as the main constituent, in particular of an iron-based alloy (hereinafter in short: iron alloy).

When implementing biodegradable implants, it is intended to control the degradability according to the intended therapy or the application of the respective implant (coronary, intracranial, renal, etc.). For many therapeutic applications it is, for example, an important target corridor that the implant loses its integrity within a time period of four weeks to six months. Here, integrity, i.e., mechanical integrity, is to be understood as the property that the implant has barely any mechanical shortcomings with respect to the non-degradable implant. This means that the implant is mechanically stable such that, for example, the collapse pressure has dropped only insignificantly, i.e., not below 80% of the nominal value. Thus, with existing integrity, the implants still meet its main function which is to ensure the penetrability of the vessel. Alternatively, integrity can be defined in that the implant is mechanically stable such that it is barely subject of any geometrical changes in its loaded state in the vessel, for example, does not collapse significantly, i.e., shows under load at least 80% of the dilatation diameter or, in case of a stent, has barely any partially fractured supporting webs.

Implants with an iron alloy, in particular ferrous stents, are producible in a particularly inexpensive and simple manner. However, for example for the treatment of stenoses, these implants lose their mechanical integrity or supporting effect only after a relatively long period of time, i.e. only after a retention period in the treated organism of approximately two years. This means that the collapse pressure for ferrous implants decreases too slow over time for this application.

A long retention period of implants can cause complications during the further treatment of the patient, namely, for example, if the dissolving implant, due to its ferromagnetic properties, does not allow or considerably affects the examination of the patient in the magnetic resonance scanner. Further, a presence of the stent in the vascular wall exceeding the necessary retention time can result in mechanical irritations therein which, in turn, can result in re-constriction of the vessel to be treated. Moreover, in case of orthopedic implants (e.g. bone plates), the formation of new bone substance can result in mechanical stress between the implant which degrades too slow and the new bone substance. This generates, in particular in children and adolescents, bone deformations or defects. For such applications it is thus desirable if the range of applications of implants, the body of which comprises at least primarily a material with the main constituent iron, can be broadened by faster degradation.

In the prior art, different mechanisms for controlling degradation of implants have already been described. They are based, for example, on inorganic or organic protection layers or their combinations which resist the human corrosive environment and the corrosion processes taking place therein. Previously known solutions are characterized in that barrier layer effects are achieved which are based on a spatial and preferably defect-free separation of the corrosion medium from the metallic medium. Said effects result in that the degradation time is extended. Thus, the degradation protection is ensured through differently composed protection layers and by defined geometrical distances (diffusion barriers) between the corrosion medium and the basic material. Further solutions in the field of the controlled degradation cause the effects of predetermined breaking points by physically changing (e.g. local cross-section changes) the stent surface (e.g. multi-layers with locally differing compositions). Other previously described methods concentrate on initiating the corrosion processes by introducing defects close to the surface and to achieve a corrosion increase in the further course by means of the increasing real surface forming thereby. Another possibility is to combine these effects from the beginning with the increase of the original surface roughness values and thus to increase the binding tendency, for example of chlorides, in such a manner that they result, in connection with increased environment humidity or in vivo, in an accelerated corrosion. However, with the above mentioned solutions it is in most cases not possible to bring the dissolution initiated by the degradation process and the resulting web breakages in the desired time window. The consequence is a degradation that starts too early or too late, or an excessive variability of the degradation of the implant.

From the printed publications EP 0 923 389 B1 or WO 99/03515 A2, or WO 2007/12430 A1, implants are known which are degradable in vivo by corrosion. The material of the known implants contains iron as main constituent and carbon in a certain predetermined concentration. The disadvantage of these alloys is that, with increasing carbon content, the binary system from carbon and iron loses significant ductility without the corrosion resistance decreasing to the same extent.

From the printed publication DE 10 2008 002 601 A1, an implant having a base body is known which consists completely or in parts of a biocorrodible iron alloy. Here, the biocoordible iron alloy has the formula Fe—P, wherein a portion of P of the alloy is 0.01 to 5% by weight and Fe as well as production-related impurities represents the remaining balance to 100% by weight of the alloy. However, the disadvantage of the known alloy is that with increased P-content, the ductility of the material decreases and it is thus more difficult to process. However, the addition of P results in an increase of the hardness of the material. Mn as an alloying constituent, which is also mentioned in the document, serves as additive for the separation of fine-phased, Pd-containing intermetallic compounds which can only be generated by alloying noble metals and/or heavy metals. However, the use of noble metals or heavy metals is often problematic and increases the cost.

In the printed publication DE 10 2004 036 954 A1, an implantable body for the intersomatic fusion (spinal fusion) is produced which is made of a bioresorbable metallic material. The metallic material comprises as main constituent alkaline metals, alkaline earth metals, iron, zinc or aluminum. As minor constituents, manganese, cobalt, nickel, chromium, copper, cadmium, lead, tin, thorium, zirconium, silver, gold, palladium, platinum, rhenium, silicon, calcium, lithium, aluminum, zinc, carbon, sulfur, magnesium and/or iron can be used. The advantage of such a material is that the material has particularly advantageous mechanical properties, in particular with respect to elasticity, deformability and stability at low mass. However, the degradation of the material is not within the desired time window.

Further examples of implants which consist of a biodegradable iron alloy are disclosed in the printed publications DE 197 31 021 A1 and WO 2007/082147 A2. In the mentioned printed publications, iron alloys with nickel and chromium are described which, in particular if they are not electropolished, release nickel ions. Nickel ions cause negative inflammatory effects not only in nickel-allergic persons. Chromium ions too, if present in a mean concentration range up to 12% by weight, can be released individually or together with other heavy metals and can potentially cause negative cell reactions. In case electropolishing is carried out, the release of nickel ions is reduced, but the degradation time is extended in a disadvantageous manner due to the formation of passivation layers.

DESCRIPTION

Therefore, the object of the present invention is to provide an implant which has a degradation of the implant within the desired target corridor, in particular within a shorter time period without the occurrence of a noteworthy ductility loss. Also, it is intended that the degradation takes place at a controllable point in time and that even implants with a complicated shape can be equipped with the desired degradation properties. Accordingly, the object of the invention is also to provide a cost-effective method for producing such an implant, The above mentioned object is solved by an implant, the body of which comprises at least predominantly a material with iron as the main constituent, wherein the material contains sulfur as first minor constituent with a concentration of more than 0.2% by weight and not more than 1% by weight, preferably not more than 0.5% by weight, and contains as second minor constituent at least one element of the group which comprises calcium, manganese and magnesium.

In the present invention, the body of the implant comprises at least a part of the implant, preferably the implant's main part which provides the mechanical integrity of the implant.

Hereinafter, the term microstructure is to be understood as the arrangement of the constituents of solid materials (solids), in particular the arrangement of the crystallites (grains), porosities, amorphous areas, and grain boundary areas of the implant body.

The advantage of the implant according to the invention with the material of the described composition is that the alloy constituents such as Mn, Mg, and Ca serve as strong sulfide formers which represent inner local elements. Local elements accelerate the degradation process by approximately the 1.5-fold of the degradation speed of the material if the same consists of stress-relieved pure iron. In a preferred embodiment, the mentioned alloy constituents can act as strong sulfide formers if they disperse during the melting process and if the particle size can be limited.

The content of said alloying elements in the material according to the invention is advantageously selected in such a manner that they reduce, in connection with sulfur, the corrosion resistance of the material considerably; however, the minimum requirements with respect to mechanical properties, which have to be met by a medical implant, are fulfilled by the material. If the contents of the mentioned elements are outside of the specified ranges, the degradation is not accelerated or the mechanical properties of the material (such as, e.g. the ultimate elongation) are changed too much.

It is also of advantage that in the material according to the invention, the content of heavy metals (except Mn) is limited to values ≤1% by weight. Thus, undesired cell reactions due to nickel and chromium can be avoided.

Another advantage of the implant according to the invention is that complex surface treatment measures for accelerating the degradation behavior are no longer necessary. However, they can optionally still be used as supporting measures for the degradation acceleration. It is also advantageous that the material of the implant according to the invention does not cause cytotoxic reactions in the body of the treated person since, for example, nickel is not used as alloying element.

Further, the corrosion process can be calculated more reliably since no gradient layers exist and the corrosion process until self-dissolution can be considered as linear. The degradation takes place in a uniform manner through the entire volume of the material.

In a preferred exemplary embodiment, the concentration of the second minor constituent calcium is at least 0.1% by weight and not more than 1% by weight, preferably more than 0.2% by weight and not more than 0.5% by weight, and/or the concentration of the second minor constituent manganese is at least 0.5% by weight and not more than 5% by weight, preferably not more than 3% by weight, and/or the concentration of the second minor constituent magnesium is at least 0.3% by weight and not more than 1% by weight, preferably not more than 0.5% by weight.

With the mentioned concentration of the respective second minor constituent, the degradability of the material is reduced; however, the mechanical properties of the material are not significantly influenced.

In a further preferred exemplary embodiment, the material of the implant body comprises, in addition, chromium as minor constituent, preferably with a concentration of 0.1% by weight to 1% by weight, particularly preferred with a concentration of 0.1% by weight to 0.5% by weight. The sulfides which also form together with chromium represent also inner local elements. In addition, chromium contributes to grain refinement so that overall by adding chromium, on the one hand, the degradation of the material is further accelerated and, on the other hand, the mechanical properties of the material are advantageously influenced by the effect of grain refinement. However, the content of chromium, as the case may be, together with other heavy metals, is not high enough to generate significant negative cell reactions caused by the release.

As main constituent of the material, the same contains preferably more than 80% by weight, particularly preferred more than 90% by weight of iron. An iron-based alloy can be produced in a particularly cost-effective manner.

It is further of advantage if the material of the implant body comprises, in addition, oxygen, preferably in a concentration of 0.05% by weight to 2% by weight, particularly preferred with a concentration of 0.05% by weight to 0.9% by weight. Together with the above mentioned minor constituents, the oxygen can effect the formation of oxidic and oxisulfidic particles in the microstructure of the material which form further inner local elements for accelerating the degradation.

In an advantageous development of the invention, the material of the implant contains in addition at least one element of the group which comprises carbon, phosphorous, vanadium, silicon, cerium, molybdenum, titanium, tungsten and zirconium. The above mentioned alloying constituents reduce the corrosion resistance of the material further by forming further intermetallic compounds, wherein the minimum requirements with respect to the mechanical properties, which have to be met by the medical implant, are still fulfilled. The reason for this is that the generated precipitations affect an additional hardening of the material. The addition of vanadium results in the formation of strength-increasing and corn refining vanadium carbides as well as the formation of vanadium oxides (vanadium(III)oxide, vanadium(V)oxide), which contribute also to the corrosion acceleration. In particular in the case of a finely dispersed distribution of said intermetallic compounds, biocompatibility problems of the compound $V_2O_5$, which is otherwise considered as a toxicological problem, are not experienced. The elements molybdenum, titanium, tungsten, and zirconium serve primarily for increasing the strength of the material.

Here, also at high cooling speed of the material during the production, in particular phosphorous has a tendency for microsegregation. Said microsegregations (zones with up to 4% by weight phosphorous) result in an increased susceptibility to corrosion.

It is in particular advantageous if the concentration of carbon is at least 0.1% by weight and not more than 0.5% by weight, preferably not more than 0.3% by weight and/or the concentration of phosphor is at least 0.05% by weight and not more than 0.5% by weight, preferably not more than 0.3% by weight, and/or the concentration of vanadium is at least 0.1% by weight and not more than 0.5% by weight, preferably not more than 0.2% by weight, and/or the concentration of silicon is at least 0.05% by weight and not more than 0.5%, preferably not more than 0.3% by weight, and/or the concentration of cerium is at least 0.05% by weight and not more than 0.5% by weight, preferably not more than 0.3% by weight.

The above mentioned contents of the alloying constituents which form sulfidic and oxidic as well as oxisulfidic microparticles are selected in such a manner that they cause precipitation hardening effects which result in sufficiently high strength properties and, at the same time, do not allow that, caused by the grain refining effects which are also present, the ultimate elongation falls below 15%. These particles, in connection with the phosphor that forms microsegregations, produce enough inner local elements which, when subject to corrosion, result in a uniform dissolution of the implant body which is accelerated in comparison to conventional iron-based alloys.

The largest portion of the sulfide, oxide or oxysulfide precipitations has a grain size in the sub-micron range (mean diameter smaller than 1 µm). For example, the precipitations are visible under the microscope in longitudinal and cross-sectional micrographs after edging with 3% alcoholic nitric acid in the form of dark spots (1 to 3 µm particle size) as Fe- and Mn-sulfides, -oxysulfides or -oxides with a total area of all spots smaller than 3% of the area of the respective micrograph. Due to the previous deformation, the precipitations can occur in a line-like preferential direction. The dark coloration results from the higher corrosion potential of these precipitations or holes which are formed by removing the particles during the edging process.

The above object is further solved by a method for producing an implant, the body of which comprises at least predominantly a material with iron as the main constituent, comprising the following steps:

a) Producing a melt with the above mentioned material composition, b) Producing a slab by cooling the melt in an adequate mold in a certain predetermined cooling rate and, preferably, carrying out at least one hot forming step for producing a semi-finished part, c) Post-processing of the semi-finished part or slab, preferably by laser cutting, until the desired shape, in particular a grid form, of the implant body is produced.

For example, cylinders, hollow cylinders, plates, ashlars, hollow ashlars or the like, in particular thin-walled tubes for stents can be produced as semi-finished parts.

The mentioned production method is very cost-effective because it includes only a few steps. Moreover, the individual production steps are easy to control so that the individual properties of the material or the implant can be produced in a simple manner. The microstructural properties of the semi-finished part or the slab and thus of the implants made from it are substantially generated during cooling of the melt; the hot forming step necessary for producing the semi-finished part is only of minor importance for adjusting the micro-structural properties.

The cooling rate used in step b) in the temperature range between 1200° C. and 700° C. is preferably at least 50 K/min and not more than 100 K/min. The primary solidification process which takes place when casting the slab, and thus the cooling rate existing at this point in time are primarily determined by the temperature of the melt, the temperature of the cold slab, the slab geometry, and the melt volume. The cooling conditions are to be selected such that no significant separation zones (segregations) are generated. This means that the melt should pass the range between liquidus and solidus as fast as possible, i.e. in a few seconds. The subsequent cooling in the solid state should take place fast enough that the temperature range between 1200° C. and 700° C. is passed within a time period of maximum 10 minutes. This is typically the case for a slab diameter of maximum 60 mm. With the production method according to the invention, the cooling of the material from the melt happens so fast that the generated particles do not agglomerate but disperse in the microstructure. This has a positive influence on the mechanical properties of the resulting implant, in particular, the ultimate elongation is not significantly changed.

To remove inhomogeneities in the microstructure generated during the cooling process, the slab can subsequently be processed by machining or turning the surface, or by deep hole drilling a core. With this procedure it is ensured that exclusively homogeneous microstructure from the central cross-section of the slab is used for subsequent processing.

The above mentioned facultative, at least one hot forming step can comprise, for example, hot forging methods, tube drawing with intermediate annealing steps, or the like. For example, a tube is produced from a slab by multi-step hot forming above the recrystallisation temperature. For the alloy according to the invention, this temperature is above 550° C. and preferably below 900° C. Due to the temperature influence, the material is not subject of a strain-hardening since at temperatures between 590° C. and 630° C. always a dynamic recrystallisation takes place. The same results in the formation of a recrystallisation structure which has a low strength but also a high deformability. Subsequently, a deep hole drilling of the rod at room temperature can be carried out. After this, further drawing steps, for example 20, take place at room temperature or a temperature of up to 100° C. After each drawing step, an intermediate annealing at a temperature of 600° C. over a period of 30 min to 60 min in air can take place, which annealing causes the microstructure to recrystallize and which re-establishes the material's deformabilty which the material had prior to the drawing step.

A preferred embodiment of the method according to the invention includes that between steps b) and c), a stress relieve annealing step is carried out which preferably takes place in a temperature range of 570° C. to 590° C., particularly preferred over a holding time of 30 minutes for a semi-finished part in the form of a thin-walled tube. Preferably, such a tube has a maximum wall thickness of approximately 200 µm. After such a stress relieve annealing step, a residual strain-hardening remains in the material; the residual stress, which thus is still present in the ferritic lattice, facilitates the corrosion as well. Scaling is avoided to the greatest possible extent.

Apart from laser cutting, step c) according to the invention can include, alternatively or additionally, mechanical deburring, corundum blasting and/or pickling in mineral acid mixtures, for example in diluted nitric acid, so that the implant body receives the desired geometry and is clean from manufacturing residues such as slag and burrs.

Onto an implant body produced in this manner, an additional coating can be applied, for example a coating containing a pharmaceutically active agent or a coating which further accelerates the degradation.

A "pharmaceutically active substance" (or therapeutically active or effective substance) in the meaning of the invention is to be understood as plant- or animal-based active agent or a synthetic active substance (medicament), or a hormone, which is used in a suitable dosage as therapeutic agent for influencing conditions or functions of the body, as substitution for naturally generated active agents in human or animal bodies such as insulin, and for eliminating pathogens, tumors, cancer cells or substances foreign to the body, or for rendering them harmless. The release of the substance in the environment of the implant has a positive effect on the healing process or acts against pathological changes of the tissue due to the surgical intervention or serves for rendering sick cells harmless in oncology.

Such pharmaceutically active substances have, for example, an anti-inflammatory and/or anti-proliferative and/or spasmolytic effect, whereby, for example, restenoses, inflammations or (vascular) spasms can be prevented.

Such substances can, for example, consist of one or more substances of the active agent group of calcium channel blockers, lipid regulators (such as, for example, fibrates), immunosuppressive agents, calcineurin inhibitors (such as, for example, tacrolimus), antiphlogistics (such as, for example, cortisone or diclofenac), anti-inflammatory agents (such as, for example, imidazoles), antiallergics, oligonucleotides (such as, for example, dODN), estrogens (such as, for example, genistein), endothelium formers (such as, for example, fibrin), steroids, proteins, hormones, insulines, cyrostatic drugs, peptides, vasodilatators (such as, for example, sartanes) and anti-proliferatively acting substances, taxoles or taxanes, here preferably paclitaxel or sirolimus (or derivates thereof).

The method according to the invention and the implant according to the invention are illustrated hereinafter by means of examples. In the course of this, all described features form the subject matter of the invention, independent of their summary in the claims or their relations.

A material with the following composition (in % by weight) is weighed:

Mn: 0.5 to 3.0
Cr: 0.1 to 0.5
V: 0.1 to 0.2

C: 0.1 to 0.3
S: higher than 0.2 to 0.5
P: 0.05 to 0.3
Mg: 0.3 to 0.5
O: max. 0.9
Se: max. 0.3
Ca: higher than 0.2 to 0.5
Ce: max. 0.3
Fe: Balance A melt of the above mentioned material composition is cast to slabs. In the range of 1200° C. to 700° C., the slabs are cooled down at a mean cooling rate of 50 K/min. The cooling conditions are determined by the slab volume, slab cross-section and the environmental conditions (room temperature and air circulation).

In the specific case, the cooling conditions are such that the temperature range between 1200° C. and 700° C. is passed also inside the slab at the latest within 3 h. Here, the slab has a wall thickness of 600 mm, an inner cross-section of 60 mm×60 mm, and a depth of 500 mm and consists of grey cast iron. This volume of 1.8 dm³ has a weight of approx. 14.0 kg. At room temperature, this amount of steel in slabs, which slabs are not additionally cooled, cools down in not more than 10 minutes from 1200° C. to 700° C. This corresponds to a mean cooling rate of approx. 50 K/min. After this, the demolding is carried out and a multi-step hot forming follows. In doing so, rods with a final diameter of 25.4 mm are produced in a plurality of steps. The multi-step hot forming takes place above the recrystallization temperature. The same lies at a temperature above 550° C. and below 900° C. for the mentioned alloy. This means that first a rod with the outer diameter of approx. 25 mm and a length of 0.5 m is produced from the slab by means of hot forging. This rod is not subject of strain hardening due to the temperature influence because at temperatures between 590° C. and 630° C. always a dynamic recrystallization takes place. This results in a recrystallization microstructure that has a low strength, but also a high deformability.

After cooling of the rod to room temperature, the deep hole drilling of the rod is carried out. For this, over the rod length of 0.5 m, a through-bore with an inner diameter of 12.7 mm is generated in the center of the rod.

The generated tube is subsequently drawn in approx. 20 drawing steps to form the final geometry of 2.00 mm outer diameter with a wall thickness of 200 μm. For this purpose, the technology of tube drawing with traveling mandrel is used. With this method, the inner diameter of the drawn tube is formed over the outer diameter of a traveling mandrel. For this, the length of the mandrel to be inserted has to correspond at least to the length of the finished tube. After each drawing step, an intermediate annealing at a temperature of 600° C. over a period of 30 min to 60 min in air takes place. After each drawing step to be carried out at room temperature or a temperature of up to ca. 100° C., the tube is detached from the mandrel by means of a rolling method and subsequently drawn off To prevent welding between the traveling mandrel and the inner diameter of the tube, the mandrel must be made of a different steel than the alloy according to the invention. Best suited is a high-alloy steel such as, e.g., 1.4841 with Cr, Ni and Si as main alloying elements.

After the final tube dimensions (outer diameter of 2 mm and wall thickness of 0.200 mm) are achieved and the traveling mandrel is drawn off, the tube is stress-relieved. This takes place at a temperature between 570° C. and 590° C. over a period of 30 min.

From the tube produced in this manner, stent-like geometries are now cut off by means of known laser cutting methods. The final contour of these stents, which is characterized by approximately square web cross-sections of approximately 100 μm×100 μm, is subsequently generated by material removing methods such as pickling in acid mixtures, corundum blasting and electropolishing. Hereby, manufacturing residues such as slag and burrs are also removed. The length of a stent produced in this manner can be between 10 mm and 30 mm. However, stents for peripheral applications can be longer.

The microstructure of the stents generated in this manner is feritic. Besides the ferrite grains, portions of a maximum of 30% perlite are also present. The average grain size is approx. 25 μm. This corresponds to a grain size number of 8 according to ASTM.

The described material composition of the stent produced in such a manner degrades approximately 1.5 times faster under body environment conditions in comparison to pure iron with 99.55% iron content. This means that a stent with a web cross-section of 100 μm×100 μm is completely degraded after approximately 18 months. A stent made of pure iron would be completely degraded only after 24 months.

Orthopedic implants such as, e.g., fixed-angle plates for the osteosynthesis of small fragments of the humerus are machined from a rod described above by means of milling and drilling. These implants have wall thicknesses of approx. 0.3 mm to 0.5 mm. Due to their relative robustness in comparison to stents, they are deburred by means of slide grinding. Optionally, electropolishing for the purpose of a further edge rounding can be used.

The degradation of an orthopedic implant produced in this manner, such as, e.g., a fixed-angle plate for the osteosynthesis, is similar to the one of the above illustrated stent. Such a fixed-angle plate degrades depending on the specific geometry and implantation site within a time period between 2 and 3 years. In contrast, a plate made of pure iron degrades completely only after at least 4 years.

Due to the corrosion tendency, which exists even under normal conditions, of the above described alloy, the above illustrated stents must be rinsed in isopropanol or acetone immediately after the last wet treatment step and must be blow-dried by means of hot air. Hereby, a premature corrosion is prevented.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implant, the body of which comprises a uniform degradation rate through the entire volume of the body when implanted, the body formed from at least predominantly a material comprising:
    iron as a main constituent;
    sulfur as first minor constituent with at a concentration of more than 0.2% by weight and not more than 1% by weight;
    a second minor constituent of at least one element selected from the group consisting of calcium, manganese and magnesium, characterized in that when the second minor constituent is calcium, the calcium is at least 0.1% by weight and not more than 1% by weight, when the second minor constituent is manganese, the manganese is at least 0.5% by weight and not more than 3% by weight, and when the second minor constituent is magnesium, the magnesium is at least 0.3% by weight and not more than 1% by weight;

oxygen at a concentration of 0.05% by weight and not more than 2% by weight;

phosphorous at a concentration of 0.05% by weight and not more than 0.5% by weight;

carbon at a concentration of 0.1% by weight and not more than 0.5% by weight; and chromium as another minor constituent with a concentration of 1% by weight, wherein the sulfides and chromium form inner local elements.

2. The implant according to claim 1, further characterized in that calcium is more than 0.2% by weight and not more than 0.5% by weight.

3. The implant according to claim 1, characterized in that the material of the implant body comprises predominantly iron, with a concentration of more than 80% by weight.

4. The implant according to claim 1, characterized in that the material of the implant contains in addition at least one element selected from the group consisting of vanadium, silicon, cerium, molybdenum, titanium, tungsten and zirconium.

5. The implant according to claim 4, characterized in that a concentration of vanadium is at least 0.1% by weight and not more than 0.5% by weight; and/or
a concentration of silicon is at least 0.05% by weight and not more than 0.5% by weight.

6. The implant according to claim 1 in a form of an intraluminal endoprosthesis.

7. The implant according to claim 3, characterized in that the iron is at a concentration of more than 90% by weight.

8. The implant according to claim 1, characterized in that the oxygen is at a concentration of 0.05% by weight to 0.9% by weight.

9. The implant according to claim 5, characterized in that the carbon is not more than 0.3% by weight; and/or
the phosphorous is not more than 0.3% by weight; and/or
the vanadium is not more than 0.2% by weight; and/or
the silicon is not more than 0.3% by weight.

10. An implant, the body of which comprises a uniform degradation rate through the entire volume of the body when implanted, the body formed from at least predominantly a material comprising:
iron as a main constituent;
sulfur as first minor constituent with at a concentration of more than 0.2% by weight and not more than 1% by weight;
a second minor constituent of at least one element selected from the group consisting of calcium, manganese and magnesium, characterized in that when the second minor constituent is calcium, the calcium is at least 0.1% by weight and not more than 1% by weight, when the second minor constituent is manganese, the manganese is at least 0.5% by weight and not more than 3% by weight, and when the second minor constituent is magnesium, the magnesium is at least 0.3% by weight and not more than 1% by weight;
oxygen at a concentration of 0.05% by weight and not more than 2% by weight;
phosphorous at a concentration of 0.05% by weight and not more than 0.5% by weight;
carbon at a concentration of 0.1% by weight and not more than 0.5% by weight; and
cerium at a concentration of least 0.05% by weight and not more than 0.5% by weight.

11. The implant according to claim 10, further characterized in that calcium is more than 0.2% by weight and not more than 0.5% by weight.

12. The implant according to claim 10, characterized in that the material of the implant body comprises predominantly iron, with a concentration of more than 80% by weight.

13. The implant according to claim 12, further characterized in that the iron is at a concentration of more than 90% by weight.

14. The implant according to claim 10, characterized in that the material of the implant contains in addition at least one element selected from the group consisting of vanadium, silicon, cerium, molybdenum, titanium, tungsten and zirconium.

15. The implant according to claim 14, further characterized in that a concentration of vanadium is at least 0.1% by weight and not more than 0.5% by weight; or a concentration of silicon is at least 0.05% by weight and not more than 0.5% by weight.

16. The implant according to claim 15, characterized in that
the carbon is not more than 0.3% by weight; and/or
the phosphorous is not more than 0.3% by weight; and/or
the vanadium is not more than 0.2% by weight; and/or
the silicon is not more than 0.3% by weight.

17. The implant according to claim 10 in a form of an intraluminal endoprosthesis.

* * * * *